United States Patent [19]

Yamanaka et al.

[11] 4,134,919
[45] Jan. 16, 1979

[54] PROCESS FOR PRODUCING MENTHONE

[75] Inventors: Tohr Yamanaka, Kamakura; Misao Yagi, Iwata, both of Japan

[73] Assignee: Takasago Perfumery Co., Ltd., Tokyo, Japan

[21] Appl. No.: 806,432

[22] Filed: Jun. 14, 1977

[51] Int. Cl.$^2$ .................. C07C 45/00; C07C 45/16
[52] U.S. Cl. .................. 260/586 P; 260/586 C; 568/829; 568/875
[58] Field of Search ............ 260/631 H, 631.5, 586 C, 260/586 P; 568/829, 875

[56] References Cited
U.S. PATENT DOCUMENTS

| | | | |
|---|---|---|---|
| 1,811,711 | 6/1931 | Blagdin | 260/631 H |
| 3,405,185 | 10/1968 | Houlihan et al. | 260/631 H |
| 3,870,761 | 3/1975 | Pasedach et al. | 260/586 C |
| 4,058,571 | 11/1977 | Budermann | 260/631 H |

OTHER PUBLICATIONS

Kogami et al., "Bull. Chem. Soc. Japan", 41, 2508–2514 (1968).
Treibs et al., "Ber", 60, 2335–2341, (1927).

*Primary Examiner*—Norman Morgenstern
*Attorney, Agent, or Firm*—Sughrue, Rothwell, Mion, Zinn and Macpeak

[57] ABSTRACT

A process for producing menthone comprising dehydrogenating citronellol in the presence of a dehydrogenation catalyst at about 150 to about 260° C in an atmosphere of hydrogen under a pressure of 0 to about 5 kg/cm$^2$. G and a process for producing menthol. Since the dehydrogenation catalyst has a hydrogenating ability, an embodiment additionally includes the ability to ultimately produce menthol in the same reactor without separating the catalyst or adding additional or another catalyst to the system by simply changing the temperature and the hydrogen pressure. Embodiments also include producing menthone and also ultimately menthol utilizing geraniol or a mixture of geraniol and citronellol as a starting material again without catalyst separation or use of additional or another catalyst.

6 Claims, No Drawings

PROCESS FOR PRODUCING MENTHONE

BACKGROUND OF THE INVENTION

1. Field of the Invention

This invention relates to a process for producing menthone, and more specifically, to a process for producing menthone, which comprises treating citronellol in the presence of a dehydrogenation catalyst at a temperature of about 150° to about 260° C in an atmosphere of hydrogen under a pressure of 0 to about 5 kg/cm$^2$.G.

2. Description of the Prior Art

Menthone is a useful compound for formulating perfumes, and can be converted to menthol by reduction.

Heretofore, synthetic levo-menthol has been produced mainly from dextro-citronellal present in natural citronella oil in an amount of 40 to 50% by weight. The residual oil remaining after the separation of dextro-citronellal is substantially a mixture of geraniol and citronellol in a ratio of 6:4 by weight and no adequate utilization of the residual oil has been found yet.

SUMMARY OF THE INVENTION

Extensive studies have now been conducted in order to utilize the residual oil, and to increase the utility of citronella oil. This work led to the achievement of the present invention.

In one embodiment of the present invention, the present invention provides a process for producing menthone in a high yield which comprises dehydrogenating citronellol in a reaction system containing a catalyst at a temperature of about 150° to about 260° C in an atmosphere of hydrogen under a pressure of 0 to about 5 kg/cm$^2$.G.

In another embodiment of the present invention, the present invention provides a process for producing menthol in good yields which comprises dehydrogenating citronellol in a reaction system containing a catalyst at a temperature of about 150° to about 260° C in an atmosphere of hydrogen under a pressure of 0 to about 5 kg/cm$^2$.G to produce menthone, and then, in the same reaction system without separating the catalyst or adding additional catalyst, hydrogenating the menthone produced by decreasing the temperature to about 110° to about 130° C and increasing the hydrogen pressure to about 10 to about 50 kg/cm$^2$.G to produce menthol.

In an even further embodiment of the invention, the invention provides a process for producing menthone which comprises hydrogenating geraniol or a mixture of geraniol and citronellol in a reaction system containing a catalyst at a temperature of about 110° to about 180° C in an atmosphere of hydrogen under a pressure of about 2 to about 10 kg/cm$^2$.G to produce citronellol, and then, in the same reaction system without separating the catalyst or adding additional catalyst, dehydrogenating the citronellol produced by increasing the temperature to about 150° to about 260° C and decreasing the hydrogen pressure to 0 to about 5 kg/cm$^2$.G to produce menthone.

In a still further embodiment of the invention, the invention provides a process for producing menthol which comprises hydrogenating geraniol or a mixture of geraniol and citronellol in a reaction system containing a catalyst at a temperature of about 110° to about 180° C in an atmosphere of hydrogen under a pressure of about 2 to about 10 kg/cm$^2$.G to produce citronellol, then, in the same reaction system without separating the catalyst or adding additional catalyst, dehydrogenating the citronellol produced by increasing the temperature to about 150° to about 260° C and decreasing the hydrogen pressure to 0 to about 5 kg/cm$^2$.G to produce menthone, and, further, in the same reaction system without separating the catalyst or adding additional catalyst, hydrogenating the menthone produced by decreasing the temperature to about 110° to about 130° C and increasing the hydrogen pressure to about 10 to about 50 kg/cm$^2$.G to obtain menthol.

DETAILED DESCRIPTION OF THE INVENTION

In each of the embodiments of the present invention described above a common step is involved and such provides the ability to obtain the advantageous results obtained in the invention. Such is shown below by the following reaction scheme.

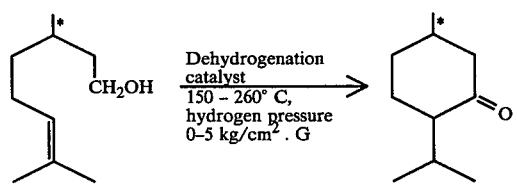

Since the optical activity on the asymmetric carbon atom shown by the symbol * is maintained in this reaction, dextro-citronellol in citronella oil is advantageously used to produce levo-menthol by the method for producing menthol through menthone obtained by the process of this invention.

All catalysts which can be used in the dehydrogenation reaction of alcohols can be used as the dehydrogenation catalysts in the process of this invention. Examples of suitable dehydrogenation catalysts include Raney-type catalysts such as cobalt, nickel, or copper, and metal oxides such as copper oxide-chromium oxide or copper oxide-zinc oxide. The catalyst has dual capacities of dehydrogenation and hydrogenation as well (e.g. see *J. Amer. Chem. Soc.*, 66, 1936 (1944)). In the presence of the catalyst, either hydrogenation or dehydrogenation can be accomplished (simply) by altering the temperature and pressure of the hydrogen employed in this invention. In the process of this invention, copper-chromium or Raney copper is preferred as the catalyst from the standpoint of catalytic activity.

The amount of the catalyst used is about 2 to about 15% by weight based on the starting citronellol, on the starting geraniol, or on the starting mixture of geraniol and citronellol.

For commercial operations, the reaction is advantageously carried out in the absence of a solvent by heating the starting material in the liquid phase in a batchwise reactor. The reaction can also be performed in the gaseous phase. In the production of menthone from citronellol, a suitable reaction temperature is about 150° to about 260° C. To reduce side-reactions with good results, the reaction is performed in an atmosphere of hydrogen under a pressure of 0 to about 5 kg/cm$^2$.G, preferably 2 kg/cm$^2$.G. The higher hydrogen pressure usually reduces the formation of by-products, and it simultaneously prevents the evolution of hydrogen. A hydrogen pressure of 0 kg/cm$^2$.G means that the reaction is carried out in an atmosphere of hydrogen in an open system. Usually, about 3 to 5 hours elapse before the evolution of hydrogen ceases and the reaction is terminated.

In the production of menthol from citronellol, menthone is produced by the same procedure described above. Subsequently, the resultant menthone is hydrogenated to menthol at a temperature of about 110° to about 130° C in an atmosphere of hydrogen under a pressure of about 10 to about 50 kg/cm$^2$.G. Usually, about 3 to 5 hours elapse before the consumption of hydrogen ceases and the reaction is terminated. In the production of menthone from geraniol or a mixture of geraniol and citronellol, initially, geraniol is hydrogenated to citronellol at a temperature of about 110° to about 180° C in an atmosphere of hydrogen under a pressure of about 2 to about 10 kg/cm$^2$.G. Usually, about 2 to 4 hours elapse before consumption of hydrogen ceases and the reaction is terminated. At higher temperatures and at higher pressures of hydrogen, a larger amount of tetrahydrogeraniol is formed. Subsequently, the reaction temperature is increased to about 150° to about 260° C and the hydrogen pressure is decreased to 0 to about 5 kg/cm$^2$.G. These processes are carried out in the same vessel. Each process is carried out successively in the presence of a specific amount of the catalyst charged initially in the reaction vessel without adding fresh catalyst or a different catalyst thereto.

The following Examples are given to illustrate the present invention more specifically.

EXAMPLE 1

Citronellol (156 g; 1 mole) and 7.8 g of a copper-chromium oxide catalyst (CuO:Cr$_2$O$_3$ = 50:50 by weight; mainly as CuCr$_2$O$_4$; less than 200 mesh, a product of Nikki Chemical Co., Ltd.) were charged into a pressure reactor, and reacted at 230° C under a hydrogen pressure of 2 kg/cm$^2$.G. In about 4 hours, the evolution of hydrogen ended. The amount of hydrogen evolved was 24 liters. The catalyst was separated from the reaction product by filtration, and the residue was distilled under reduced pressure to afford 140 g of a fraction having a boiling point of 82° to 90° C/12 mmHg. This fraction was a mixture of menthone and iso-menthone in a ratio of 6:4 by weight. The theoretical yield was 90%. Also, 7.7 g of thymol boiling at 108° to 110° C/12 mmHg was obtained.

EXAMPLE 2

A copper-aluminum (Cu:Al = 50:50 weight ratio) alloy was leached with a sodium hydroxide aqueous solution according to the W-5 method to form an aqueous dispersion of Raney copper. The water in the aqueous dispersion was replaced with ethyl alcohol, and then the ethyl alcohol, was replaced by 156 g (1 mole) of citronellol. In this way, the amount of the catalyst was adjusted to 10% by weight based on the citronellol. Subsequently, the procedures described in Example 1 were repeated under the same conditions as disclosed in Example 1. The results obtained were similar to those obtained in Example 1.

EXAMPLE 3

The procedures of Example 1 were repeated except that a copper-zinc catalyst (CuO:ZnO = 50:50 by weight; a product of Nikki Chemical Co., Ltd.) was used instead of the copper-chromium catalyst described in Example 1. The results obtained were similar to those obtained in Example 1.

EXAMPLE 4

Copper-chromium oxide (7.8 g; CuO:Cr$_2$O$_3$ = 50:50 weight ratio) was added to 156 g of a mixture of citronellol and geraniol (41 wt% citronellol, 59 wt% geraniol, $[\alpha]_D^{20}$ = + 1.00) separated and purified from citronella oil. The mixture was reacted at 170° to 180° C for 2 hours in an atmosphere of hydrogen under a pressure of 3 kg/cm$^2$.G to afford citronellol ($[\alpha]_D^{20}$ = + 0.8). The reaction temperature was increased to 260° C, and the reaction was further carried out for 3 hours under a hydrogen pressure of 2 to 2.5 kg/cm$^2$.G to afford menthone (comprising 60 wt% of menthone and 40 wt% of iso-menthone). The specific rotation of the menthone as the enol acetate was +22.9 ($[\alpha]_D^{20}$). This specific rotation means that 80% of the optical purity present in the citronellol in the starting material was retained in the menthone in the product.

When the resulting menthone was reacted subsequently at a temperature of 120° C under a hydrogen pressure of 25 kg/cm$^2$.G for 5 hours in the same reaction system, menthol (comprising 50 wt% of menthol, 21 wt% of iso-menthol and 29 wt% of neo-menthol) was obtained. The product was column-chromatographed to separate pure menthol ($[\alpha]_D^{20}$ = +19.5; optical purity 40% (80% based on citronellol in the starting material)).

The optical purity of the menthone mixture as the enol acetate was determined from the following formula.

$$\frac{\text{(Specific Rotation Measured)} \times \text{(Content of Menthone)}}{\text{(Specific Rotation } ([\alpha]_D^{20} = +67.6) \text{ of a Pure Enol Acetate from Menthone)}}$$

(see Agr. Biol. Chem., 27, 433, 1963)

EXAMPLE 5

156 g of purified citronellol ($[\alpha]_D^{20}$ = +2.3) was reacted with 7.8 g of copper-chromium oxide (CuO:Cr$_2$O$_3$ = 50:50) at 260° C for 2 hours under a hydrogen pressure of 2.5 kg/cm$^2$.G to afford menthone (menthone 59 wt%, iso-menthone 41 wt%). The product was converted to the enol acetate having a specific rotation, $[\alpha]_D^{20}$, of +55. The optical purity of the product was 80% of that of the starting material. The product was hydrogenated in the same manner as described in Example 4. From the resulting menthol mixture, menthol was isolated. The menthol had a specific rotation, $[\alpha]_D^{20}$, of +39 and an optical purity of 80%.

EXAMPLE 6

At the end of the reaction in Example 1, the reaction product was further reacted at 120° C under a hydrogen pressure of 25 kg/cm$^2$.G without separating the catalyst from the reaction product. In 5 hours, the absorption of hydrogen ended. Distillation of the reaction mixture under reduced pressure afforded 158 g of an isomeric menthol mixture. By gas chromatographic analysis, the product was found to comprise 35 wt% of neo-menthol, 25 wt% of neo-iso-menthol, 35 wt% of menthol, and 5 wt% of iso-menthol.

While the invention has been described in detail and with reference to specific embodiments thereof, it will be apparent to one skilled in the art that various changes and modifications can be made therein without departing from the spirit and scope thereof.

What is claimed is:

1. A process for producing menthone which comprises dehydrogenating citronellol in a reaction system containing a Raney-type catalyst or a metal oxide catalyst at a temperature of about 150° to about 260° C in an atmosphere of hydrogen under a pressure of 0 to about 5 kg/cm$^2$.G.

2. The process as claimed in claim 1, wherein the amount of the catalyst is about 2 to about 15% by weight based on the weight of the citronellol.

3. The process as claimed in claim 1, wherein the hydrogen pressure is 2 kg/cm$^2$.G.

4. A process for producing menthol which comprises dehydrogenating citronellol in a reaction system containing a Raney-type catalyst or a metal oxide catalyst at a temperature of about 150° to about 260° C in an atmosphere of hydrogen under a pressure of 0 to about 5 kg/cm$^2$.G to produce menthone as claimed in claim 1, and then, in the same reaction system without separating the catalyst or adding additional catalyst, hydrogenating the menthone produced by decreasing the temperature to about 110° to about 130° C and increasing the hydrogen pressure to about 10 to about 50 kg/cm$^2$ to produce menthol.

5. A process for producing menthone which comprises hydrogenating geraniol or a mixture of geraniol and citronellol in a reaction system containing a Raney-type catalyst or a metal oxide catalyst at a temperature of about 110° to about 180° C in an atmosphere of hydrogen under a pressure of about 2 to about 10 kg/cm$^2$.G to produce citronellol, and then, in the same reaction system without separating the catalyst or adding additional catalyst, dehydrogenating the citronellol produced by increasing the temperature to about 150° to about 260° C and decreasing the hydrogen pressure to 0 to about 5 kg/cm$^2$.G to produce menthone as claimed in claim 1.

6. A process for producing menthol which comprises hydrogenating geraniol or a mixture of geraniol and citronellol in a reaction system containing a Raney-type catalyst or a metal oxide catalyst at a temperature of about 110° to about 180° C in an atmosphere to hydrogen under a pressure of about 2 to about 10 kg/cm$^2$.G to produce citronellol, then, in the same reaction system without separating the catalyst or adding additional catalyst, dehydrogenating the citronellol produced by increasing the temperature to about 150° to about 260° C and decreasing the hydrogen pressure to 0 to about 5 kg/cm$^2$.G to produce menthone as claimed in claim 1, and, further, in the same reaction system without separating the catalyst or adding additional catalyst, hydrogenating the menthone produced by decreasing the temperature to about 110° to about 130° C and increasing the hydrogen pressure to about 10 to about 50 kg/cm$^2$.G to produce menthol.

* * * * *